United States Patent [19]

Borch et al.

[11] Patent Number: 5,294,430

[45] Date of Patent: *Mar. 15, 1994

[54] USE OF DITHIOCARBAMATES TO TREAT MYELOSUPPRESSION

[75] Inventors: Richard F. Borch, Pittsford, N.Y.; Therese K. Schmalbach, Newton, Mass.

[73] Assignee: University of Rochester, Rochester, N.Y.

[*] Notice: The portion of the term of this patent subsequent to Jul. 30, 2010 has been disclaimed.

[21] Appl. No.: 922,688

[22] Filed: Jul. 30, 1992

Related U.S. Application Data

[60] Continuation-in-part of Ser. No. 700,218, May 13, 1991, abandoned, which is a division of Ser. No. 418,549, Oct. 10, 1989, Pat. No. 5,035,878, and a continuation-in-part of Ser. No. 665,975, Mar. 7, 1991, abandoned, which is a continuation-in-part of Ser. No. 586,305, Sep. 21, 1990, abandoned, which is a continuation-in-part of Ser. No. 418,549, Oct. 10, 1989, Pat. No. 5,035,878, which is a continuation-in-part of Ser. No. 243,405, Sep. 12, 1988, Pat. No. 4,938,949.

[51] Int. Cl.$^5$ .................. A61K 39/00; A61K 31/27
[52] U.S. Cl. ...................................... 424/10; 514/476
[58] Field of Search ........................... 424/10; 514/476

[56] References Cited

U.S. PATENT DOCUMENTS

| | | | |
|---|---|---|---|
| 4,053,587 | 10/1977 | Davidson et al. | 424/10 |
| 4,137,248 | 1/1979 | Gale et al. | 424/10 |
| 4,148,885 | 4/1979 | Renoux et al. | 424/162 |
| 4,426,372 | 1/1984 | Borch | 424/10 |
| 4,529,543 | 7/1982 | Renoux et al. | 260/410 R |
| 4,562,275 | 12/1985 | Speer et al. | 556/7 |
| 4,581,224 | 4/1986 | Borch | 424/10 |
| 4,594,238 | 6/1986 | Borch | 424/10 |
| 4,645,661 | 2/1987 | Schonbaum et al. | 424/10 |
| 4,680,308 | 7/1987 | Schwartz et al. | 514/192 |
| 4,721,096 | 1/1988 | Naughton et al. | 128/1 |
| 5,035,878 | 7/1991 | Borch | 424/10 |

OTHER PUBLICATIONS

Innes et al. J. National Cancer Institute 42:1101-1114 (1969).
Prasad et al. Cell & Chromosome Res. 6(3):82-84 (1983).
B. Rosenberg, Cancer Treatment Reports 63: 1433-1438 (1979).
G. D. Thorn et al *The Dithiocarbamates and Related Compounds*, (Chapter 2, pp. 7-42) Elsevier, New York (1962).
J. S. Greenberger, in *Hematopoiesis*, pp. 203-242, D. W. Golde (ed.) Churchill Livingstone, Edinburgh (1984).
T. K. Schmalbach et al., Cancer Res. 49: 2574-2577 (1989).
R. Qazi et al., J. Natl. Cancer Inst. 80: 1486-1488 (1988).
L. H. Williams et al., Exp. Hematol. 16: 80-87 (1988).
D. A. Juckett et al., AACR Abstracts 25: 322 (Abstract No. 1274) (1984).
D. L. Bodenner et al., Cancer Res. 46: 2751-2755 (1986).
R. G. Evans et al., Cancer Res. 44: 3686-3690 (1984).
J. D. Khandekar, Res. Communications Chem. Path. and Pharmacol. 40: 55-66 (1983).
A. Gringeri et al., AACR Abstracts, p. 371, Abstract No. 1471 (1984).

(List continued on next page.)

Primary Examiner—Frederick E. Waddell
Assistant Examiner—Gregory Hook
Attorney, Agent, or Firm—Merchant, Gould, Smith, Edell, Welter & Schmidt

[57] ABSTRACT

A process for preventing or ameliorating the myelosuppression which can occur in a mammal such as a human cancer patient being treated with a platinum-free antineoplastic drug is provided, comprising administering an effective dosage of a dithiocarbamate compound to said mammal, preferably subsequent to administration of the cytotoxic drug.

17 Claims, No Drawings

U.S. PATENT DOCUMENTS

I. M. Pannacciulli et al., *Br. J. Cancer* 59: 371 (1989).

H. Prasad et al., *Cell and Chromosome Res.* 6: 82–84 (1983).

J. R. M. Innes et al., *J. National Cancer Institute* 42: 1101–1114 (1969).

R. C. Gamelli et al., *Cancer Chemother. Pharmacol.* 16: 153–155 (1986).

F. W. Sunderman, Sr., *Annals Clinical Res.* 3: 182–185 (1971).

M. M. Jones et al., *Cancer Chemother. Pharmacol.* 17: 38–42 (1986).

A. Gringeri et al., *Cancer Research* 48: 5708–5712 (1988).

R. I. Freshey, *Culture of Animal Cells, A Manual of Basic Technique* (2nd ed.), pp. 284–288, Alan R. Liss, Inc. (1987).

M. Y. Gordon et al., *Internatl. J. Cell Cloning* 1: 429–439 (1983).

Allalunis-Turner et al., *Int. J. Radiat. Oncol. Biol. Phys.* 10: 1569–1573.

Remington's Pharmaceutical Sciences, A. Osol, ed., Mack Publishing Co. (16th ed. 1980) at pp. 1083–1085, 1090–1091.

Sigma Chemical Co., 1381 (1989).

K. Ikebochi et al., *PNAS USA*, 84, 9035 (1987).

*The Merck Index* (11th ed.), p. 610, S. Budavani (ed.), Merck & Co., Inc., Rahway, N.J. (1989).

*The Physicians Desk Reference* (41st ed.), pp. 768–769, E. R. Barnhart (publ.), Medical Economics Co., Oradell, N.J. (1987).

T. Schamlbach et al., *Blood*, 76 (10 Suppl. 1) 164a (1990).

USE OF DITHIOCARBAMATES TO TREAT MYELOSUPPRESSION

CROSS-REFERENCE TO RELATED APPLICATIONS

This application is a continuation-in-part of U.S. patent application Ser. No. 7/700,218, filed May 13, 1991, now abandoned, which is a divisional of U.S. patent application Ser. No. 7/418,549, filed Oct. 10, 1989 (U.S. Pat. No. 5,035,878); and this application is a continuation-in-part of U.S. patent application Ser. No. 7/665,975, filed Mar. 7, 1991, now abandoned, which is a continuation-in-part of U.S. patent application Ser. No. 07/586,305, filed Sep. 21, 1990, now abandoned, which is a continuation-in-part of U.S. patent application Ser. No. 07/418,549, filed Oct. 10, 1989 (U.S. Pat. No. 5,035,878), which is a continuation-in-part of U.S. patent application Ser. No. 07/243,405, filed Sep. 12, 1988 (U.S. Pat. No. 4,938,949).

BACKGROUND OF THE INVENTION

At least as far back as the early 1970s, it was found that dithiocarbamates and their dimers (e.g., disulfiram) are clinically useful compounds of relatively low toxicity toward mammals. Various sulfur-containing compounds including sodium diethyldithiocarbamate (NaDDTC) have been suggested as immunostimulant medicines. See U.S. Pat. No. 4,148,885 (Renoux et al.), issued Apr. 10, 1979. Also, dithiocarbamates or their dimers have been used to inhibit the undesirable side effects of platinum compounds such as the square planer platinum (II) complexes used as antineoplastic agents. See U.S. Pat. Nos. 4,426,372 (Jan. 17, 1984), 4,594,238 (Jun. 10, 1986), and 4,581,224 (Apr.8, 1986), all issued to R. F. Borch. The platinum compounds useful as antineoplastic agents are not limited to platinum (II) compounds, because it has been found that platinum (IV) compounds can be administered in much the same manner as platinum (II) compounds, apparently because these six-ligand complexes break down in vivo to square planar complexes of the platinum (II) type.

The Borch method of, for example, U.S. Pat. No. 4,426,372, has been shown to be effective in clinical trials. That is, this method substantially reduces the side effects of platinum-containing drugs. These side effects include both kidney toxicity and bone marrow toxicity. For 5 mg/kg of intravenously administered platinum compound in mice, the amount of dithiocarbamic "rescue agent" is likely to be in the range of 100 mg/kg to 400 mg/kg (intravenously) and can range as high as 750 mg/kg (intraperitoneally), also in mice. A dosage of less than 50 mg/kg of body weight of dithiocarbamate is not likely to be fully effective in providing relief from or prevention of kidney damage.

Although pharmaceutically acceptable dithiocarbamic compounds such as sodium diethyldithiocarbamate (NaDDTC) and disulfiram have relatively high $LD_{50}$ values and are not considered highly toxic to mammals, there are scattered reports in the literature regarding strange behavior exhibited by rats or mice injected with NaDDTC. The true import of this literature became fully apparent during clinical trials of NaDDTC as a "rescue agent"i.e., as an agent for the reduction of side effects from the administration of platinum compounds. These clinical trials demonstrated that human patients given dosages of NaDDTC effective for "rescue" purposes (e.g., dosages on the order of 50–150 mg/kg of body weight) experienced extremely unpleasant effects which caused them to feel panic and discomfort. It was necessary to develop a technique of administration of the NaDDTC whereby the patient is sedated prior to receiving the dithiocarbamate.

All available evidence indicates that the panic reaction to dithiocarbamates resulting from dosages of, for example, 50–150 mg/kg is not the result of any life-threatening process occurring in the body of the patient, nor is there any evidence of permanent or chronic effects or damage resulting from NaDDTC administration. After the course of dithiocarbamate administration has been completed, patients returned to normal and no sequellae of the panic reaction are observed. Moreover, it presently appears that some hydroxy-substituted analogs of NaDDTC may be even less toxic than NaDDTC itself. Nevertheless, further improvement in the treatment of toxic side effects of useful cytotoxic compounds is desirable.

As noted previously, much less is known about treatments for bone marrow toxicity. Some anti-cancer drugs, both platinum-containing and platinum-free, can seriously damage the blood-forming function of the bone marrow—an effect sometimes referred to as myelosuppression. Among the drugs causing significant myelosuppression effects are the toxin-derivative, etoposide, certain heavy metal complexes, as well as cytotoxic antibiotics and antibiotic derivatives, antimetabolites, alkaloid-type anti-tumor agents, and alkylating agents. Although dithiocarbamates have been shown to effectively inhibit the myelosuppression caused by platinum-containing antineoplastic drugs, such as carboplatin or cisplatin, little is known about their interaction with platinum-free antineoplastic drugs.

Therefore, a need exists to counteract or prevent the myelosuppression caused by platinum-free cytotoxic, antineoplastic drugs, particularly myelosuppression caused by etoposide.

SUMMARY OF THE INVENTION

It has now been discovered that dithiocarbamic compounds of the formula (I):

wherein $R^1$ and $R^2$ are the same or different ($C_1$–$C_6$) alkyl groups, ($C_3$–$C_6$) cycloalkyl groups or ($C_5$–$C_6$) heterocycloalkyl groups, or one of $R^1$ and $R^2$, but not both, can be H, or $R^1$ and $R^2$, taken together with the N atom, can be a 5-6 membered N-heterocyclic ring which is aliphatic or aliphatic interrupted by a ring oxygen or second ring nitrogen, and M is H or one equivalent of a pharmaceutically acceptable cation, in which case the rest of the molecule is negatively charged, or M is

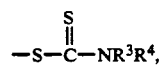

wherein $R^3$ and $R^4$ are defined in the same manner as $R^1$ and $R^2$, are surprisingly effective for the treatment of damage to the blood-forming function of the bone marrow of a living mammal (myelosuppression) caused by the administration of a platinum-free cytotoxic drug, as during treatment of a human cancer patient. Preferably, the compounds of formula I are administered in very low doses and/or are administered after the administration of the cytotoxic drug. Preferably, the platinum-free cytotoxic drug is selected from the group consisting of an antimetabolite (such as 5-fluorouracil), an alkaloid and a DNA-synthesis inhibitor (such as etoposide).

Amounts of dithiocarbamic compound in excess of 30 mg/kg of body weight of small mammals (e.g. mice) are not needed in this invention, and would be very excessive for large mammals such as humans. At least some beneficial response to the dithiocarbamic compound is observable even in small mammals at dosage levels in the microgram/kg range. Thus, a suitable dosage unit according to this invention can be in the range of about 0.001 to 30 mg per kilogram of body weight of the mammal, more preferably at about 0.003–10 mg/kg of body weight.

As will be explained subsequently, guidelines for converting these dosage units into mg/m$^2$ have been discovered, both for large mammals, such as humans, and small mammals, such as mice. In principle, mg/m$^2$ dosing is equivalent in all species, including both large and small mammals. It has also been found that the gap between a suitable mg/kg dosage unit for a small mammal and a suitable mg/kg dosage unit for a human is somewhat less than might have been predicted by a skilled pharmacologist.

These very low dosages are believed to be well below stoichiometric levels and bear more resemblance to amounts at which catalysts are employed. Surprisingly, improvement in the blood-forming function of normal bone marrow is rather minimal when the dithiocarbamic compounds of this invention are administered to a healthy mammal. However, very significant improvements in bone marrow function are observed when the bone marrow of the mammal is threatened with damage by the administration of etoposide. However, because there may be some time delay involved in observing the beneficial effects of this invention, it is possible to administer the dithiocarbamic compound more or less simultaneously with the etoposide. Typically, the dithiocarbamic compound will be administered prior to, and continued after the platinum-free cytotoxic drug has been given to the patient.

The preferred dithiocarbamic compounds used in this invention are those dithiocarbamates of the aforementioned formula (I), $R_1R_2NCSSM$, wherein M is a pharmaceutically acceptable cation, such as sodium, potassium, ammonium and the like; and $R_1$ and $R_2$ are lower aliphatic groups. The preferred route of administration of these compounds (particularly when M is a metallic cation) is parenteral, e.g., intravenous, and a suitable unit dosage can be dissolved, suspended, or otherwise combined with a pharmaceutically acceptable carrier such as an aqueous medium, e.g., a physiological salt solution. In the case of the dimers (e.g., disulfiram), which are far less water soluble, the preferred route of administration is oral, e.g., as tablets, encapsulated in hard or soft gelatin, or the like.

DETAILED DESCRIPTION

Myelosuppression (toxicity to the blood-forming cells of the bone marrow) is a serious and frequently dose-limiting side effect of most anticancer drugs used in the oncology clinic today. Because these are rapidly dividing cells, they are particularly susceptible to the toxic effects of the drug used to control diseases of cell proliferation. The stem cell is the most primitive of the bone marrow cells; it represents less than 0.1% of the cells of the marrow, yet it is capable of differentiating to produce progenitor cells for all of the blood cell lines (red cells, lymphocytes, granulocytes, and platelet precursors). The stem cell is also a self-replenishing cell in that it can undergo division to generate additional stem cells. Although stem cells have been only recently specifically isolated and characterized, and then only in mice, an estimate of their numbers can be obtained using the spleen colony assay (CFU-S). Maintenance of an appropriate population of stem cells is obviously critical to survival of mammals and perhaps other organisms.

The granulocyte precursor is one of the most important and frequently damaged progenitor cell in the bone marrow. Its clinical importance lies in the role that the granulocyte plays in fighting infections. Patients with markedly reduced granulocyte counts resulting from cancer chemotherapy are highly susceptible to infection from a variety of organisms and, if bone marrow function does not recover quickly enough, they can succumb to infection rather than the primary malignancy for which they have been receiving treatment. The granulocyte precursor derives from differentiation of a stem cell; this precursor can undergo subsequent amplification and differentiation to produce a mature granulocyte. The granulocyte precursor is more abundant in the marrow than the stem cell, and its numbers can be estimated using the colony-forming units-granulocyte/-macrophage (CFU-GM) assay.

TREATABLE BONE MARROW DAMAGE

Most of the discussion which follows is related to the use of dithiocarbamates to protect against the bone marrow toxicity of platinum-free anti-cancer drugs. However, it will be understood that the method of this invention can find application whenever the blood-forming function of the bone marrow of a living mammal has been damaged. As noted previously, clinical use of the method and dosage units of this invention can be carried out in combination with known platinum-free antitumor agents and can be more or less simultaneous with (or even previous to) the administration of the antitumor agent, although typically the antitumor agent will be administered first. It is generally desirable that, when the antitumor agent is administered first, the dithiocarbamate is given to the treated mammal within 6 or 8 hours.

Mechanistic studies done in connection with this invention reveal that anticancer drugs which inhibit tumor growth through interference with DNA, such as etoposide which inhibits the action of topoisomerase, are significantly modulated in their effect upon bone marrow when the dithiocarbamate is administered after the anti-cancer drug, e.g., in the case of etoposide, at less than two hours afterward. The mechanism of bone marrow protection provided by the dithiocarbamic compounds is different from that involved in the reversal of other toxicities (e.g., kidney toxicity) and is not dependent upon stoichiometric displacement of platinum from biochemical structures. For example, dithiocarbamates such as sodium diethyldithiocarbamate (DDTC) do not alter the number of bone marrow cells proliferating in vivo in the absence of myelotoxic insult.

As noted previously, antineoplastic agents and treatment techniques are a particularly important cause of myelosuppression. As noted above, the drugs which have adverse effects upon blood formation (e.g., bone marrow toxicity) fall into several categories including cytotoxic antibiotics isolated from cultures of various species of Streptomyces and derivatives of such antibiotics (bleomycin, daunorubicin, dactinomycin, doxorubicin hydrochloride), antimetabolites such as 5-fluorouracil, 5-azacytidine, methotrexate, cytarabine, mercaptopurine, and thioguanine; alkaloid-type compounds including alkaloids extracted from natural sources such as the periwinkle plant and similar herbs (vincristine sulfate, vinblastine sulfate), DNA synthesis inhibitors and DNA crosslinkers which can be, for example, non-haloalkyl alkylating agents such as (a) the ethylenimines, i.e., thiotepa, (b) alkylsulfonates, i.e., busulfan, or (c) certain heavy metal complexes (such as the platinum complexes discussed previously). Another class of alkylating agents contains compounds containing the 2-chloroethyl group (typically, a 2-chloroethyl group attached to a nitrogen atom), i.e., lomustine. There are compounds presently in clinical use which fall into none, or into more than one of these categories. In some cases, the mode of action of an antineoplastic drug is unknown, e.g., in the case of dacarbazine.

"Adriamycin" (Doxorubicin hydrochloride) is an example of Streptomyces-produced antibiotic derivative which is known to cause bone marrow suppression effects, primarily of leukocytes. Hence, careful hematologic monitoring is required when this drug is being administered to produce regression in neoplastic conditions.

The antineoplastic "alkylating agents" which have the 2-chloroethyl (i.e., the beta-chloroethyl) group, typically attached to a nitrogen atom, include derivatives of L-amino acids, derivatives of steroids, monocyclic compounds, are aliphatic amine derivatives, and urea derivatives (including nitrosourea derivatives). Compounds of the nitrosourea type typically have the following formula:

Cl—CH₂CH₂—N(NO)—CO—NH—R* wherein R* is an organic group such as an aliphatic or cycloaliphatic radical or a second 2-chloroethyl group. One widely used compound of this type is 1-3-bis(2-chloroethyl)-1-nitrosourea, also known as BCNU or BiCNU or carmustine.

In alkylating antineoplastic drugs containing the 2-chloroethyl group, the bis-(2-chloroethyl)-amino functional group is particularly common, e.g., as in chlorambucil or cyclophosphamide. This bis-substituted group has the formula (ClCH₂CH₂)₂N— and can be substituted directly on an aliphatic chain or an aromatic or cycloaliphatic or heterocycloaliphatic ring (or indirectly, whereby N is part of a carbamate linkage or the like). The so-called "nitrogen mustard" derivatives typically contain the bis-(2-chloroethyl)-amino group and can be highly toxic if not carefully administered. These bis-substituted alkylating agents are believed to act by cross-linking DNA, thus preventing the linked strands from separating for replication.

Of the non-alkylating cytotoxic antineoplastic drugs that appear to exert their effects predominantly on cellular DNA, but which are neither alkylating agents (haloalkyls) or heavy metal complexes, etoposide, which is useful against lung cancer and refractory testicular tumors, is of particular importance. It is currently commercially available as VEPESID® etoposide from Bristol-Meyers. Etoposide is a semisynthetic derivative of podophyllotoxin; (4'-demethylepipodophyllotoxin-9-[4,6-0-(R)-ethylidene-β-D-glucopyranoside). Etoposide is discussed extensively The Merck Index, S. Budavani, ed., Merck & Co., Inc., Rahway, N.J. (11th ed. 1989) at page 610 and in the Physicians Desk Reference, E. R. Barnhart, pub., Medical Economics Co., Oradell, N.J. (41st ed. 1987) at pages 768–769, the disclosures of which are incorporated by reference herein.

The usual dose is 50–100 mg/m²/day, days 1–5 or 100 mg/m²/day, days 1, 3 and 5 every 3–4 weeks preferably in combination with other drugs approved for use in the condition to be treated. As discussed below, this dose corresponds to about 1.3–2.75 mg/kg/day. For example, the platinum (II) and (IV) compounds are often used in combination with etoposide. For a discussion of the types of platinum-containing drugs contemplated by Borch for use in combination with dithiocarbamic compounds, see (in addition to the three Borch patents) U.S. Pat. No. 4,053,587 (Davidson et al.), issued Oct. 11, 1977; U.S. Pat. No. 4,137,248 (Gale et al.), issued Jan. 30, 1979; U.S. Pat. No. 4,562,275 (Speer et al.), issued Dec. 31, 1985; U.S. Pat. No. 4,680,308 (Schwartz et al.), issued Jul. 14, 1987, and similar references appearing in both the patent and scientific literature, e.g., the series of papers regarding platinum treatment of tumors and resulting side effects in Cancer Treatment Reports, 63, 1433 (1979). The compound "cisplatin" (cis-dichlorodiammine platinum [II]) is very effective against testicular and ovarian tumors but has been found to have myelosuppressive effects in 25–30% of patients treated with this drug. More recent developments in platinum (II) and platinum (IV) anticancer drugs have produced compounds which are not only very effective against tumors but are also substantially free of side effects other than myelosuppression. Cisplatin, on the other hand, has significant kidney toxicity effects as well as bone marrow toxicity Of the nitrogen-containing platinum monodentates and bidentates myelosuppression can occur when the ligands include ammonia, diaminocyclohexane and its derivatives, alkylene and diamines (e.g., ethylenediamine), alkyl-substituted amines, $C_3$- and $C_5$-cycloalkyl amines, and the like. Suitably selected tetravalent Pt complexes can behave like Pt(II) complexes after administration to a living organism. Removal of axial ligands in vivo accounts for the Pt(II)-like activity, at least to some extent. A particular preferred species of Pt(IV) complex is chlorohydroxy-isopropylamine-platinum ("CHIP"). "CHIP" like other "second-generation" platinum-containing therapeutic agents is low in kidney toxicity compared to the "first generation" agents but, unfortunately, is high in bone marrow toxicity.

Various Pt(II) compounds of demonstrated antitumor utility, e.g., "TNO-6" and "CBDCA" (see U.S. Pat. No. 4,137,248) also showed increased bone marrow toxicity. These otherwise desirable Pt(II) compounds can be characterized by the formula:

$(R'NH_2)(R''NH_2)Pt(X^1)(X^2)$ where $X^1$ and $X^2$ are the same or different and are halogen, OH, water, carboxyl, sulfato, or sulfate, or, taken together, the residue of a polycarboxylic acid; $X^1$ and $X^2$ preferably are $SO_3H$ or $—CO_2—$, particularly as the residue of a polycarboxylic acid such as 1,1-cyclobutane-dicarboxylic acid, trimellitic acid, etc; R' and R" are the same or different and are halogen or an aliphatic group, or taken together, the aliphatic residue of a heterocyclic moiety which includes both N-atoms.

DITHIOCARBAMIC COMPOUNDS

The term "dithiocarbamic compounds" including the preferred dithiocarbamates, as used in this application is intended to refer to compounds containing the functional group $R_1R_2N\text{-CS-S-}$, wherein $R_1$ and $R_2$ are the same or different and represent different aliphatic groups, cycloaliphatic groups or heterocycloaliphatic groups, e.g., ($C_1$–$C_6$) alkyl, ($C_5$–$C_{10}$)cycloalkyl or five- to ten-membered heterocyclic groups, unsubstituted or substituted by hydroxyl. One of the two groups, $R_1$ and $R_2$, but not both, can be hydrogen. Alternatively, $R_1$ and $R_2$, taken together with the N-atom, can be a 5- or 6-membered N-heterocyclic ring which is aliphatic ($-(CH_2)_n-$) or aliphatic interrupted by a ring oxygen or a second ring nitrogen.

When the group $R_1R_2N\text{-CS-S-}$ is part of a dimer such as disulfiram, the dangling valence bond is linked to a group of the formula $\text{-S-CS-NR}_3R_4$, wherein $R_3$ and $R_4$ are defined in the same manner as $R_1$ and $R_2$. When the group $R_1R_2N\text{-CS-S-}$ is an anion, the cation can be of the ammonium-type or can be derived form a monovalent or divalent metal such as an alkali or alkaline earth metal, cations which provide good water solubility and low toxicity being preferred, e.g., $Na^+$, $K^+$, $Zn^{++}$ and the like. In the case of the dithiocarbamic acids, the group $R_1R_2N\text{-CS-S-}$ is linked to a hydrogen atom which is ionizable, particularly at a pH above about 5. Since the dithiocarbamic acids are not very stable in vitro, it would appear to be only marginally operative, and not advantageous, to use the dithiocarbamic acid form of the myelosuppression treatment agents of this invention. However, these acids are generally soluble in polar organic solvents such as alcohol, and they would have some tendency to form stable alkali metal salts in body fluids.

Dithiocarbamates and related compounds have been reviewed extensively in a work by G. D. Thorn et al. entitled "The Dithiocarbamates and Related Compounds," Elsevier, N.Y., 1962. As explained in Chapter 2 of Thorn et al., the preparation of dithiocarbamates is very simple. The compounds of the formula $R_1R_2\text{NCSSH}$ or $R_1R_2\text{NCSSNa}$ can be formed by reaction of carbon disulfide with a secondary amine, typically in alcoholic or aqueous solution. The usual practice is to carry out this reaction in the presence of NaOH, so that the sodium dithiocarbamate salt is formed. Thus, for example, sodium dimethyl dithiocarbamate is formed from $CS_2$, NaOH and dimethylamine. See Thorn et al., page 14, and the references cited therein. Other typical dithiocarbamic compounds disclosed and characterized in Thorn et al. include: N-methyl,N-ethyldithiocarbamates, hexamethylenedithiocarbamic acid, sodium di(beta-hydroxyethyl)dithiocarbamate, various dipropyl, dibutyl and diamyl dithiocarbamates, sodium N-methyl,N-cyclobutylmethyl dithiocarbamate, sodium N-allyl-N-cyclopropylmethyldithiocarbamate, cyclohexylamyldithiocarbamates, dibenzyl-dithiocarbamates, sodium dimethylene-dithiocarbamate, various pentamethylene dithiocarbamate salts, sodium pyrrolidine-N-carbodithioate, sodium piperidine-N-carbodithioate, sodium morpholine-N-carbo-dithioate, alpha-furfuryl dithiocarbamates and imidazoline dithiocarbamates.

Another interesting type of dithiocarbamate which appears to have significant bioavailability and biocompatibility includes compounds wherein $R_1$ of the structure $R_1R_2N\text{-CS-S-}$ is a hydroxy-substituted or, preferably, a (bis to penta) polyhydroxy-substituted lower alkyl group having up to 6 carbon atoms. For example, $R_1$ can be $\text{HO-CH}_2\text{-CHOH-CHOH-CHOH-CHOH-CH}_2\text{-}$. In such compounds, $R_2$ can be H or lower alkyl (unsubstituted or substituted with one or more hydroxyl groups). Steric problems can, of course, be minimized when $R^2$ is H, methyl, or ethyl. Accordingly, a particularly preferred compound of this type is an N-methylglucamine dithiocarbamate salt, the most preferred cations of these salts being sodium or potassium.

The term "lower" (as in "lower alkyl" or "lower aliphatic"), as used in this discussion, refers to radicals having one to six carbon atoms. Water solubility and/or biocompatibility problems can be greatly increased when the number of carbon atoms exceeds six. Of the unsubstituted alkyl groups, the ethyl radical appears to provide a high level of water solubility coupled with relatively low toxicity. Nevertheless, compounds such as sodium diethyldithiocarbamate (NaDDTC) are not necessarily well tolerated by humans and other mammals (even smaller mammals) when administered at levels above 50 mg/kg of body weight. Patients complain of flushing and tightness in the chest during infusion of NaDDTC, and they develop symptoms of acute anxiety. These symptoms subside rapidly and without sequelae after the infusion is stopped, and the symptoms can be alleviated somewhat (but not abolished) by pretreatment sedatives. In the scientific literature, there are occasional references to analogous effects in rats, and these effects are sometimes referred to as the "rat rage" syndrome. A major advantage of this invention is that the "rat rage" syndrome can be avoided entirely due to the surprising efficacy of dosage units of this invention.

Other preferred dithiocarbamates include the alkali or alkaline earth metal salts wherein the anion is di-n-butyldithiocarbamate, di-n-propyldithiocarbamate, pentamethylenedithiocarbamate, and tetramethylene dithiocarbamate. Generally speaking, the greater the solubility in polar solvents (particularly in aqueous media), the more convenient the administration of the dithiocarbamic myelosuppression treatment agent can be, because parenteral administration is particularly preferred in the method of this invention, and solutions (particularly aqueous solutions) are more convenient to administer than suspensions.

For this reason, the monomeric dithiocarbamic compounds are preferred over the dimeric analogs. Disulfiram is commercially available and has been used in the treatment of alcoholism to help the patient remain in a state of self-imposed sobriety. This treatment is carried out by oral administration of disulfiram in tablet form. Disulfiram has relatively low solubility in polar solvents, whereas diethyldithiocarbamate monomeric salts and hydroxysubstituted alkyl dithiocarbamate monomeric salts are highly soluble in water, e.g., in molar quantities, and are also soluble in alcohol.

Other parenteral modes of administration can be used, e.g., intramuscular injection or introduction through the intraperitoneal route. Oral administration can also be employed to administer dithiocarbamates in accord with the present method. However, the dosage units of this invention are most effective by the intravenous route.

DOSAGE UNITS AND FORMS

It is very common in pharmacology to express dosage units in mg/kg (i.e., mg/kg of body weight) or, if a continuing series of doses over many days is contemplated, mg/kg per day. A mg/kg dosage unit is reasonably constant for any given species of mammal. However, an average effective dose can vary from species to species, due to differences in metabolic rates. Smaller mammals such as rats and mice metabolize drugs (convert the drugs to other compounds in vivo) more effectively than larger mammals such as dogs and humans. Theoretical studies of drug metabolic rates in general tend to confirm that there is a rough inverse correlation between drug metabolic rate and the surface area of the body of the mammal. In principle, then, a dosage expressed in $mg/m^2$ would be roughly equivalent in all species, regardless of body area, i.e., an $ED_{50}$ of 100 $mg/m^2$ in a human would also be 100 $mg/m^2$ in a mouse. To convert mg/kg to $mg/m^2$, one multiplies by a constant for the desired species which is a function of the surface area of a member of that species, thus:

Dose in $mg/m^2$ = Constant x dose in mg/kg. The constant for human, dog, rat and mouse species are, respectively; 37, 20, 5.2, and 3.0. Expressed in relative terms, the human constant is almost twice the dog constant (1.9), the human constant is over 7 times the rat constant, and the human constant is 12.3 times the mouse constant. The dosage unit for NaDDTC administered to mice to ameliorate the kidney toxicity of Cisplatin (750 mg/kg, preferably >200 mg/kg) works out to be, for example, 3.0×200 mg/kg=600 $mg/m^2$, more typically 3.0×300 mg/kg=900 $mg/m^2$. Theoretically, then, the typical human dosage unit would be 900 $mg/m^2$ divided by 37=about 25 mg/kg. In other words, theory would predict that the human dose in mg/kg would be about one-twelfth of the dose for mice. In actual practice, however, it has been found that the human dose of NaDDTC can be as much as a sixth to a third, e.g., one-fourth of the dose for mice; hence, a dose in mice of, for example, 30 mg/kg works out in practice to be 5 to 10 mg/kg, most typically 7.5 mg/kg for humans. In the present invention, a dosage of 0.3 mg/kg (1 $mg/m^2$) can provide some useful effect in humans and has even been observed to show some bone marrow-restoring effect in mice. A reliable effective dose range is, for example, about 1.0 to about 145 $mg/m^2$, more preferably 130 $mg/m^2$, regardless of species. For all species, the dosage of 130 $mg/m^2$ is ample and may be unnecessarily large. Suitable dosage units can be less than 90 $mg/m^2$ or, if desired, less than 75 $mg/m^2$. For humans, dosage units in mg/kg are best calculated by dividing the mg/kg dose for mice by about 4 (instead of by 12.3). Accordingly, a dose for mice of, say, 30 mg/kg would work out to about 7.5 mg/kg in a human, and a dose for mice of 10 mg/kg would work out to about 2.5 mg/kg in a human.

In the treatment of myelosuppression, dithiocarbamic treatment agents of this invention exhibit a rather typical sigmoidal logarithmic dose-response curve, but the placement of this curve with respect to the dose and response axes is surprising. To obtain a typical logarithmic dose-response curve, the percent of surviving stem cells in the test animals is indicated by the ordinate, and the dosage is indicated in 10-fold intervals ($log_{10}$ dose units) with respect to the abscissa. The resulting plot shows that optimal bone marrow protection can be obtained at dosages well below 50 mg/kg of body weight, and even at well below 30 mg./kg. A response can be observed at extremely low dosages (above sub-microgram/kg levels but still below 3 $\mu g/kg$, e.g., about 1 $\mu g/kg$), and significant protection appears to be obtained, even in mice, at dosages as low as 3 $\mu g/kg$, i.e., 0.003 mg/kg. Dosages approaching 30 mg/kg (even in mice) appear to be unnecessarily high in the context of the method of this invention, hence a preferred range for a dosage unit of this invention is about 0.3 to 10 mg/kg of body weight of the mammal. The "flat" portion of the sigmoidal curve appears to be reached at dosages as low as 0.3 mg/kg, but it can be desirable to exceed this dosage level in order to provide assurance that efficacy will be high. A particularly preferred upper limit for the human dose appears to be about 10 mg/kg, more preferably 3.0 or even 2.5 mg/kg. When the dosage units are in $mg/m^2$, a useful range is, for example, 1–200 $mg/m^2$, more preferably about 1–75 $mg/m^2$, as explained previously.

A particularly preferred form of a dosage unit of this invention is obtained by dissolving a dithiocarbamate salt in an aqueous medium (e.g., normal saline), measuring out a dosage unit in the range of 0.001 to 30 mg per kilogram of body weight of the mammal to be treated, and sealing the resulting dosage unit in a vial (e.g., a glass or plastic vial) adapted for use in a conventional intravenous administration technique. Alternatively, the dosage unit can be dissolved in a conventional plastic intravenous drip bag, in which case the dosage unit can be diluted with an aqueous solution of a typical intravenous administration fluid. (The potential chelating or complexing effects of the dithiocarbamic compound should be taken into account, with respect to such fluids.)

Alternatively, a dosage unit of the dithiocarbamic compound can be extended with a standard solid pharmaceutically acceptable extender (e.g., mannitol) and packaged in dosage unit form for solution later on in a fluid suitable for intravenous administration. Adjuvants, excipients, and the like can be included.

A particularly preferred unit dosage of this invention comprises about 0.01 to about 10 mg./kg of the dithiocarbamic myelosuppression treatment agent, the treatment agent being dissolved in a liquid pharmaceutically acceptable carrier comprising an aqueous medium. Other suitable pharmaceutically acceptable carriers are available to those skilled in the art.

As noted previously, clinical use of the method and dosage units of this invention can be more or less simultaneous with (or even previous to) the administration of the antitumor agent, although typically the antitumor agent such as etoposide will be administered first, and the dithiocarbamic compound administered soon thereafter. It is generally desirable that, when etoposide or 5-fluorouracil is administered first, the dithiocarbamate is given to the treated mammal before about 1.5 to 2 hours have elapsed.

The principle and practice of this invention is illustrated in the following non-limiting Examples.

EXAMPLE I $BDF_1$ mice were used and the drugs were administered by intravenous (iv) injection in the tail vein. Sodium diethyldithiocarbamate (DDTC) was administered at various dosages 3 hours after administration of an anticancer drug. Bone marrow cells were harvested 24 hours after anticancer drug treatment (21 hours after NaDDTC). Toxicity to stem cells was evaluated using the spleen colony (CFU-S) assay; toxicity to granulocyte progenitors was evaluated using an in vitro clonogenic (CFU-GM) assay. To provide controlled studies, mice were randomly divided into four groups of four animals each; one group served as a no-treatment control, one group received DDTC alone (the "DDTC group"), one group received anticancer drug alone (the "drug-only group"), and one group received anticancer drug followed by DDTC 3 hours later (the "drug and DDTC group"). Twenty-four hours after drug treatment, the mice were killed by cervical dislocation, the femurs were removed, and the marrow cells were flushed out of the bone and counted.

For the CFU-S assay, $5-15 \times 10^4$ cells were injected via the tail vein into recipient mice that had just received a bone marrow lethal dose of radiation. Twelve days after injection of donor marrow cells, the mice were killed by cervical dislocation, the spleens were removed, and the colonies of cells growing on the surface of the spleen were counted. The data are normalized to represent the number of colonies formed/$10^5$ cells injected and are reported as the percent of colonies formed compared to the control group.

For the CFU-GM assay, $2-4 \times 10^4$ bone marrow cells from the treated groups were plated on soft agar. After incubating for 7 days, the colonies containing at least 50 cells were counted; in representative experiments, the colonies were removed and the cell type determined. The data are reported as the percent of colonies formed compared to the control group.

The data obtained from the DDTC group and the no-treatment group tends to confirm that DDTC has little or no stimulant effect upon healthy bone marrow in vivo. That is, DDTC has negligible effects on the stem cell and granulocyte precursor populations in normal mouse bone marrow. The colony counts for the DDTC group were within 10% of no-treatment group values for both CFU-S and CFU-GM in all cases. In the drug-only group, dose-dependent toxicity toward both CFU-S and CFU-GM was observed for carmustine (BCNU) and adriamycin. In the drug and DDTC group, DDTC provided significant protection against BCNU toxicity to both stem cells and granulocyte progenitors at all doses of BCNU tested. In the case of adriamycin, reduction of toxicity was observed at all doses but was less impressive at the highest adriamycin dose tested.

The situation in the case of mitomycin (an anti-cancer drug of the antibiotic type) is more complicated because it is particularly difficult to prevent or reverse the myelosuppressive effects of this drug.

Very good results were obtained when the drug + DDTC group was given carboplatin (a platinum-containing anticancer drug) followed by various doses of DDTC. Carboplatin given to the drug-only group resulted in mice having CFU-S values which were only 10% of the control group level. When the CFU-S assay shows 30% or more of the value of the control (no treatment) group, this is considered indicative of very good activity against myelosuppression. The 30% level in the drug +DDTC group was achieved with an iv dose of 30 mg/kg of NaDDTC, but 40% of the control CFU-S level was also achieved with an iv dose of only 0.3 mg./kg of NaDDTC.

In the experiments summarized in Table I (which were conducted according to the procedure described above), the dose of NaDDTC was 300 mg/kg of body weight, which appears to be excessive, but which illustrates the efficacy of dithiocarbamate, vis-a-vis damage from platinum-free drugs. Both in Part A (drug=BCNU) and in Part B (drug=adriamycin), data are given for the "DDTC group" the "drug-only group" and the "drug and DDTC group". These data are set forth in Table I, below.

TABLE I

EFFECT OF NaDDTC ON DRUG-INDUCED MYELOSUPPRESSION

| Drug Dose (mg/kg) | Mouse Group | CFU-S (%) | CFU-GM (%) |
|---|---|---|---|
| Part A Drug: BCNU | | | |
| — | DDTC | 102 ± 2 | 102 ± 1 |
| 20 | Drug-only | 47 ± 6 | 83 ± 2 |
| 20 | Drug and DDTC | 57 ± 12 | 99 ± 2 |
| — | DDTC | 101 | 103 ± 2 |
| 40 | Drug-only | 30 ± 1 | 43 ± 2 |
| 40 | Drug and DDTC | 50 ± 1 | 83 ± 2 |
| — | DDTC | 114 | 102 ± 2 |
| 65 | Drug-only | 19 ± 2 | 25 ± 1 |
| 65 | Drug and DDTC | 49 ± 11 | 64 ± 1 |
| Part B Drug: Adriamycin | | | |
| — | DDTC | 106 | 102 |
| 18 | Drug-only | 38 ± 6 | 37 ± 6 |
| 18 | Drug and DDTC | 52 ± 11 | 45 ± 2 |
| — | DDTC | — | 102 ± 1 |
| 24 | Drug-only | 40 ± 2 | 32 ± 1 |
| 24 | Drug and DDTC | 52 ± 6 | 42 ± 2 |
| — | DDTC | — | 102 |
| 32 | Drug-only | 29 ± 8 | 20 ± 5 |
| 32 | Drug and DDTC | 57 ± 7 | 28 ± 2 |

EXAMPLE II

DDTC FOLLOWING ETOPOSIDE AND 5-FU TREATMENT

A. DRUG TREATMENT

Drug solutions were prepared immediately prior to use and filter sterilized prior to administration to BDF mice via the lateral tail vein. Etoposide (VP-16) was obtained from Bristol Meyers-Squibb and formulated according to the manufacturer's instructions. It was administered at a dose of 32 mg/kg. Five-fluorouracil was administered at a dose of 50 mg/kg. Sodium diethyldithiocarbamate (DDTC) was dissolved in sterile water at 5 mg/ml concentration and administered at a dose of 30 mg/kg. Mice were randomly assigned to one control and four treatment groups (3 per group). The control group was injected with saline. All treatment groups received etoposide; one group received saline 1 hr after etoposide treatment, and the other 3 groups received DDTC 1, 2, or 3 hours after etoposide treatment, or 1 or 3 hours after 5-FU treatment. The mean weight of the three mice per group was used to calculate the volume of the injectate.

B. PREPARATION OF BONE MARROW CELLS

Twenty-four hours after etoposide administration, the mice were sacrificed by cervical dislocation, and the femurs from each group were removed and placed in ice cold medium or buffer. Bone marrow cells were harvested by flushing the marrow from these femurs with 1 ml of ice cold medium or buffer. A single cell suspension of the pooled femoral marrow was made by gentle, repeated pipetting of the sample. The number of nucleated bone marrow cells obtained was determined by counting an aliquot of the cell suspension (following lysis with Turk's solution) using a hemocytometer, and the viability was assessed via dye exclusion. The cell concentration was then adjusted by dilution with additional medium or buffer to the desired density.

C. GRANULOCYTE/MACROPHAGE PROGENITOR CELL (GM-CFC) ASSAY

The volume of cell suspension needed to achieve a final density of $2 \times 10^4$ viable nucleated cells/ml was then added to minimum essential medium, alpha-modifications ($\alpha$-MEM) supplemented with 0.8% (w/v) methylcellulose, 20% (v/v) fetal bovine serum, 1% (w/v) deionized bovine serum albumin, 10% (v/v) pokeweed mitogen-stimulated spleen cell-conditioned medium (PWM-SCCM), and 50 $\mu$g/ml gentamicin. One ml aliquots were plated in quadruplicate in 35 mm petri plates. These cultures were incubated in a 37° C., fully humidified 5% $CO_2$ incubator for 7 days. Granulocyte/macrophage colonies (>50 cells/colony) were counted with the aid of a dissecting microscope. The morphology of the cells in the colonies was verified by removing the colonies from the media with a finely drawn pipet, resuspending each colony in 0.4 ml of media ($\alpha$-MEM or Fischer's) supplemented with 1-5% serum (horse or FBS), spinning the colony onto a slide with a Cytospin centrifuge (500 rpm for 5 min), and staining with Wright-Giemsa stain. The mean number of colonies counted in the four cultures from each group was expressed as the percent of the mean number of colonies in colonies/$10^5$ cells plated). The data reported are the mean $\pm$S.E. from three separate experiments.

D. RESULTS

Treatment with etoposide or with 5-FU in the absence of resulted in GM-CFC colonies that numbered 65% or 30.7% of control, respectively, indicating substantial toxicity at this dose. When DDTC was administered one hour after etoposide treatment, the GM-CFC increased to 89% of control values. When DDTC was given one hour after 5-FU treatment, the GM-CFC increased to 54.8% of control values. The importance of timing for DDTC administration was apparent when DDTC was given 2 or 3 hours after etoposide; the results (66% and 62% of control, respectively) showed that, in contrast to DDTC administration at one hour, there was no beneficial effect. Likewise, administration of DDTC three hours after 5-FU had no beneficial effect. These results are summarized in the following Table II, below.

TABLE II

| Treatment | Etoposide-DDTC Interval (hour) | GM-CFC % Control |
|---|---|---|
| Etoposide | — | 64.7 ± 2.6 |
| Etoposide + DDTC | 1 | 89.1 ± 2.4* |
| Etoposide + DDTC | 2 | 66.3 ± 1.9 |
| Etoposide + DDTC | 3 | 62.1 ± 4.4 |
| 5-FU | — | 30.7 ± 1.8 |
| 5-FU + DDTC | 1 | 54.8 ± 3.7** |
| 5-FU + DDTC | 3 | 25.8 ± 0.4 |

*Significantly different from etoposide alone (p < .05).
*Significantly different from 5-FU alone (p < .05).

EXAMPLE III

The following experiments were conducted to demonstrate the production of bone marrow cell growth factor(s) with DDTC.

A. MATERIALS AND METHODS

Cis-diammine(cyclobutanedicarboxylato)platinum (II), or "CBDCA" was obtained from Johnson-Matthey, Inc. (Malvern, Pa.). Sodium diethyldithiocarbamate (DDTC) was obtained from Sigma Chemical Company (St. Louis, Mo.). Fischer's medium, $\alpha$-MEM, L-glutamine, pokeweed mitogen, sodium bicarbonate (7.5% solution), gentamicin, penicillin/streptomycin solution, and antibiotic/antimycotic solution were purchased from GIBCO (Grand Island, N.Y.). Horse serum and fetal bovine serum were purchased from Hyclone Laboratories (Logan, Utah). Salmonella typhosa lipopolysaccharide B (LPS) was purchased from Difco Laboratories (Detroit, Mich.). Methylcellulose (4A premium grade) was provided by Dow Chemical Company (Midland, Mich.). Falcon Petri plates and microscope slides were obtained from Fisher Scientific Company (Springfield, N.J.). All other plastic culture supplies and test tubes were obtained from VWR (Rochester, N.Y.).

B. EXPERIMENTAL ANIMALS

Male 6- to 8-week-old C57BL/6J x DBA/2J mice were obtained from The Jackson Laboratories (Bar Harbor, Me.). Mice were housed 10/cage in plastic cages and allowed food and water ad libitum. All mice were acclimated for at least 7 days; the animals were then killed by cervical dislocation and both femurs and tibias were harvested for these experiments.

C. ESTABLISHMENT OF MURINE LONG-TERM BONE MARROW CULTURES (LTBMC).

Long-term bone marrow cultures were established according to J. S. Greenberger, in *Hematopoiesis*, D. W. Golde, ed., Churchill Livingstone, Edinburgh (1984) at pages 203-242. One ml of growth medium [Fisher's medium (pH 7.0) supplemented with 25% horse serum, 100 U/ml penicillin G, and 100 $\mu$g/ml streptomycin] was used to aseptically flush marrow cells from one murine tibia and femur into a flask containing 9 ml of growth medium. The cultures were maintained in a fully humidified incubator, 5% $CO_2$ atmosphere, at 33° C. Weekly feeding was performed by replacement of the spent medium and nonadherent cells with 10 ml of fresh medium. Where specified, the medium also contained $10^5$ M hydrocortisone sodium hemisuccinate, to facilitate development and maintenance of the adherent cells.

Cultures of the stromal bone marrow cells were established in the same fashion. However, the supplemental horse serum (25%) was replaced with 20% fetal bovine serum as a supplement to Fischer's medium (pH 7.0) and the antibiotic solution as described above. These culture conditions do not allow survival of colony-forming units-granulocyte/erythrocyte/macrophage/megakaryocyte (CFU-GEMM) or granulocyte/macrophage progenitor cells (GM-CFC) (confirmed by removing the adherent cells from three cultures and testing for the presence of CFU-GEMM or GM-CFC). In all other respects, the cultures were initiated and maintained as described above.

D. GRANULOCYTE/MACROPHAGE PROGENITOR CELL (GM-CFC) ASSAY

This assay was carried out using the method of T. K. Schmalbach et al., *Cancer Res.*, 49, 2574 (1989), but with the following modifications. Bone marrow cells were harvested from untreated mice, and in the LTBMC experiments, the PWM-SCCM was replaced with 500 μl of supernatant harvested from the drug treated (or control) LTBMC. Granulocyte/macrophage colonies >50 cells were counted on day 7 with the aid of a dissecting microscope. The morphology of the cells in the colony was verified by removing the colonies from the media with a finely drawn pipet, resuspending the colony in 0.4 ml of media (α-MEM or Fischer's) supplemented with 1–5% serum (horse or FBS), spinning the colony onto a slide with a Cytospin centrifuge (500 rpm for 5 min.), and staining with Wright-Giemsa stain. Positive (maximally stimulating amounts of PWM-SCCM included in the culture medium) and negative (no mitogen added) controls were included with each assay. The formation of colonies under these conditions was indicative of colony-stimulating activity in the LTBMC supernatants.

E. DETERMINATION OF COLONY STIMULATING ACTIVITY (CSA) IN MEDIA OF DRUG-TESTING LTBMC

The cultures were allowed to grow for 5 to 6 weeks prior to experimentation. Twelve cultures were randomly divided into four groups (control, DDTC, CBDCA, and CBDCA followed by DDTC), 3 cultures per group. Drug solutions were prepared immediately prior to use with unsupplemented medium and filter sterilized. CBDCA (300 μM in 10 ml medium) was applied to CBDCA- and CBDCA/DDTC-treated groups while the control and DDTC-treated groups received medium only. Cultures were replaced in the incubator for one hour. The medium/drug solution was then removed and DDTC (300 μM in 10 ml medium) was added to DDTC and CBDCA/DDTC groups, while the control and CBDCA cultures received medium only. After one hour, these solutions were removed, and 10 ml of supplemented Fischer's medium were added to each culture. At the specified time, this medium, along with any nonadherent cell groups, was removed, and the cells were pelleted by centrifugation (800×g for 5 min.). The supernatants were subsequently evaluated for colony-stimulating activity in the GM-CFC assay as described above.

A similar procedure was used to determine the response of drug-treated cultures exposed to mitogen stimulation. In these experiments, Salmonella typhosa lipopolysaccharide B (5 μg/ml) was added in place of drug to the supplemented Fischer's medium following drug treatment. At the specified times, the medium was removed and tested for colony-stimulating activity as described above.

The CSA production stimulated by various doses of DDTC was determined by treating triplicate cultures with the specified concentration of DDTC or media alone for one hour. This solution was then replaced with supplemented Fischer's medium. Forty-eight hours later, the medium was removed, non-adherent cells were pelleted by centrifugation, and the supernatant was tested for colony-stimulating activity.

F. RESULTS

After 5 weeks, the LTBMC were treated with DDTC with or without prior treatment with CBDCA. At various times, the supernatants were removed and the colony-stimulating activity (CSA) of each supernatant was assessed by using it to replace the pokeweed mitogen-stimulated spleen cell conditioned medium in the GM-CFC assay. Basal levels of granulocyte/macrophage colony-stimulating activity (CSA) in control supernatants varied with each experiment, since differences in serum constituents are known to affect the ability of LTBMC to support hematopoiesis. Enhancement of CSA in three separate experiments is summarized in Table III.

TABLE III

Enhancement of GM-CSA by Supernatants Removed from LTBMC

| Removal Time (hr) | Treatment Agent* | | | |
|---|---|---|---|---|
| | CBDCA | DDTC | CBDCA + DDTC | Pokeweed Mitogen (PWM)** |
| 24 | 1.0 ± 0.1 | 3.9 ± 0.7 | 2.6 ± 0.4 | 8.6 ± 1.9 |
| 48 | 1.2 ± 0.2 | 3.4 ± 0.7 | 3.0 ± 0.6 | 6.6 ± 2.2 |
| 72 | 1.1 ± 0.1 | 3.3 ± 0.5 | 2.9 ± 0.5 | 8.2 ± 2.2 |
| 96 | 0.8 ± 0.1 | 4.7 ± 1.7 | 3.9 ± 1.1 | 8.9 ± 3.1 |
| Combined | 1.0 ± 0.1 | 3.8 ± 0.5 | 3.1 ± 0.4 | 8.1 ± 1.2 |

*Results are ratio of colonies/$10^5$ cells using supernatants from treated LTBMC compared to control LTBMC treated with growth medium alone, Mean ± SEM from three experiments at each time point.
**Positive control.

CSA was augmented almost 4-fold in supernatants from DDTC-treated cultures, and this level represented about 50% of the maximal stimulation observed with conditioned medium (PWM-SCCM). CBDCA had no significant effect on CSA either alone or when added just prior to DDTC treatment. DDTC enhanced CSA at concentrations from 100–1000 μM. These concentrations are readily achieved in the plasma of patients treated with DDTC, as demonstrated by R. Qazi et al., J. Nat. Cancer Inst., 80, 1486 (1988).

EXAMPLE IV

To determine whether or not DDTC is enhancing production of a factor(s) that stimulates progenitor cells, two different agents known to have CSA were evaluated in combination with DDTC. Addition of hydrocortisone hemisuccinate to the DDTC-treated cultures neither enhanced or diminished DDTC-induced CSA compared to treatment with DDTC alone (data not shown). Supernatants from cultures treated with a maximally stimulating concentration of LPS (5 μg/ml) induced formation of 195 colonies/$10^5$ cells. Neither DDTC, CBDCA, nor the combination of CBDCA and DDTC significantly changed the CSA of these supernatants (190–210 colonies/$10^5$ cells). These results demonstrate that DDTC is inducing production of colony-stimulating factor(s) that is not additive with respect to stimulation by either hydrocortisone or LPS.

EXAMPLE V

The hematopoietic microenvironment is believed to play a pivotal role in the regulation of blood cell production and differentiation. Stromal cells are most likely responsible for elaborating the colony-stimulating factors that regulate the LTBMC system. Thus, LTBMC containing stromal cells (including monocytes/macrophages) were established by the method of L. H. Williams et al., Exp. Hematol., 16, 80 (1988). The cells growing in these cultures were plated in standard clonogenic assays, and no progenitor or stem cell growth was observed, thereby confirming the absence of hematopoietic progenitor cells. Untreated supernatants from these cultures had greater CSA compared to those obtained from the complete LTBMC, and DDTC treatment enhanced CSA approximately twofold compared to untreated cultures. Again, CBDCA treatment had no significant effect on untreated or DDTC treated cultures. These data indicate that DDTC stimulation of CSA is most pronounced during the first 24 hours after treatment. This was confirmed by comparing the CSA of supernatants collected over varying time intervals. CSA was significantly enhanced by DDTC in supernatants collected between 0-8 hours and 8-24 hours after DDTC treatment but was not significantly different from untreated supernatants obtained during later time intervals (data not shown).

The results of Examples III-V indicate that DDTC modulates hematologic toxicity by inducing stromal cell production of a factor or factors that stimulate hematopoiesis. Although DDTC stimulates proliferation of both stem cells and GM progenitors in vivo only after damage or inhibition of the blood-forming cells of the bone marrow has occurred, e.g., via pretreatment with a myelotoxic drug, CSA was increased by exposure to DDTC alone in vitro. Treatment of LTBMC with a cytotoxic concentration of CBDCA had no effect on CSA, and CBDCA neither enhanced nor inhibited the DDTC response in vitro. These results are consistent with a mechanism in which DDTC augments rather than initiates a proliferative response. The response is presumably initiated by cytotoxic drug in vivo and by the addition of fresh medium in vitro. The involvement of stromal cells in the DDTC response may also account for the variable results observed with different cytotoxic agents, because direct toxicity to stromal cells would be expected to reduce the DDTC response.

These results represent the first example of bone marrow proliferation resulting from induction of colony-stimulating factor(s) by a small molecule. Although the identity of the factor(s) responsible for the CSA induced by DDTC is not known, several cytokines may be potential candidates. For example, granulocyte/macrophage colony-stimulating factor (GM-CSF) and granulocyte colony-stimulating factor (G-CSF) may play a role in the DDTC response, but their effects may be secondary to release of another cytokine such as IL-1$\alpha$, IL-1$\beta$, IL-6, IL-3, or mixtures thereof. The concentration of tumor necrosis factor has also been found to be increased in culture.

Thus, the production of one or more growth factors (which factor or factors have G/M cell CSA) can be accomplished in vitro by adding to the culture medium of an in vitro, established bone marrow culture a growth factor-stimulating amount of a previously described compound of the formula I ($R^1R^2N(CS)SM$)(preferably about 0.1 to about 1.0 millimole, e.g., about 0.2 to 0.5 millimole, of the compound per liter of culture medium), separating the compound from the thus-treated culture, adding fresh culture medium to the thus-treated culture, and permitting the concentration of growth factor or factors to build up in the fresh medium. This concentration appears to reach a peak in 8 to 72-96 hours (e.g., 24-48 hours) and then declines, because the growth factor or factors are continuously subject to consumption or utilization by the treated culture. The growth factor or factors can then be isolated by removing the fresh medium from the treated bone marrow culture, and performing conventional steps used to concentrate and purify cytokines.

Accordingly, this invention also contemplates in vivo or in vitro stimulation of one or more bone marrow cell growth factors (having G/M cell CSA) via the exposure of bone marrow cells to small amounts of one or more of the previously-described dithiocarbamic compounds of the formula (I), preferably of the formula $R^1R^2N(CS)SM$, wherein $R^1$, $R^2$ and M are as defined above. Hence, this invention can provide a surprisingly simple alternative to the use of cytokines such as the interleukins, and other highly complex cell growth stimulating factors which are difficult to synthesize in quantity without resorting to the use of genetically-engineered organisms. Therefore, the stimulation and proliferation of other cells which has been accomplished using IL-1 or IL-2 in the past, can be accomplished using thiocarbamic compounds of formula I. For example, the stimulation and proliferation of LAK cells or of T-helper cell populations can also be accomplished or augmented in accord with the present invention.

The administration of DDTC or other dithiocarbamic compounds of the formula I, preferably of the formula $R^1R^2N(CS)SM$, for this purpose is particularly attractive in view of the low toxicity of these compounds, their high solubility in ordinary pharmaceutically acceptable media such as water, and their extraordinary efficacy in stimulating G/M cell CSA at very low doses. Dosage units of this invention are ideal for time-intensive as opposed to time-diffusive use, i.e., essentially single-dose use. That is, the entire dose, undivided or divided into less that 5 or 10 increments, is administered over a very short period of time, e.g., less than 24 hours and preferably less than 8 hours (most preferably by a single injection) and preferably only in response to—and within 24 hours (preferably within 8 hours) of—an insult to the bone marrow (such as a radiation treatment or an anticancer treatment). This time-intensive use is easily distinguishable from continuous dosing and is particularly different from long-term regimens in which a compound is given repeatedly over a period of several days or weeks or in some other time-diffusive manner typically involving small doses.

All of the documents cited hereinabove, including the patents and patent applications listed under the heading "Cross-Reference to Related Applications"are incorporated by reference herein. The invention has been described with reference to various specific and preferred embodiments and techniques. However, it should be understood that many variations and modifications may be made while remaining within the spirit and scope of the invention.

What is claimed is:

1. A method for the treatment of myelosuppression resulting from a toxic side effect of a platinum-free cytotoxic drug selected from the group consisting of an antimetabolite, and a DNA synthesis inhibitor, administered to a human, said process comprising administering to said human an effective dosage of about 0.001 to 10 mg/kg of the body weight of said human, of a compound of the formula (I):

wherein $R^1$ and $R^2$ are the same or different ($C_1$–$C_6$) alkyl groups, ($C_3$–$C_6$) cycloalkyl groups or ($C_5$–$C_6$) heterocycloalkyl groups, or one of $R^1$ and $R^2$, but not both, can be H, or R and $R^2$, taken together with the N atom, can be a 5-6 membered N-heterocyclic ring which is aliphatic or aliphatic interrupted by a ring oxygen or second ring nitrogen, and M is H or one equivalent of a pharmaceutically acceptable cation, in which case the rest of the molecule is negatively charged, or M is

wherein $R^3$ and $R^4$ are defined in the same manner as $R^1$ and $R^2$.

2. The method of claim 2 wherein M is one equivalent of a pharmaceutically acceptable cation.

3. The method of claims 1 or 2 wherein $R^1$ and $R^2$ are the same or different $(C_1-C_6)$alkyl or $(C_3-C_6)$cycloalkyl.

4. The method of claims 1 or 2 wherein $R^1$ and $R^2$ are both $(C_1-C_6)$alkyl.

5. The method of claim 4 wherein $R^1$ and $R^2$ are both ethyl.

6. The method of claim 5 wherein the compound of formula I is sodium diethyldithiocarbamate.

7. The method of claim 1 wherein the cytotoxic drug is an antimetabolite.

8. The method of claim 7 wherein the antimetabolite is 5-fluorouracil.

9. The method of claim 1 wherein the cytotoxic drug is a DNA-synthesis inhibitor.

10. The method of claim 9 wherein the DNA synthesis inhibitor is etoposide.

11. The method of claim 1 wherein the compound of formula I is administered intravenously.

12. The method of claim 11 wherein the compound of formula I is administered in combination with a pharmaceutically acceptable aqueous medium.

13. The method of claim 1 wherein the compound is administered orally.

14. The method of claims 1, 7, 8, 9, or 10 wherein the compound of formula I is administered after the administration of the cytotoxic drug.

15. The method of claim 14 wherein the compound of formula I is administered within 2 hours after administration of the cytotoxic drug.

16. The method of claim 14 wherein about 0.003-10 mg/kg of the body weight of the human of the compound of formula I is administered.

17. The method of claim 1 wherein the human is a cancer patient.

* * * * *

UNITED STATES PATENT AND TRADEMARK OFFICE
CERTIFICATE OF CORRECTION

PATENT NO. : 5,294,430
DATED : March 15, 1994
INVENTOR(S) : Borch et al.

It is certified that error appears in the above-indentified patent and that said Letters Patent is hereby corrected as shown below:

In column 13, line 36, after "of " please insert --DDTC--

In column 14, line 47, please delete "$10^5$" and insert --$10^{-5}$--

Signed and Sealed this

Fourteenth Day of October, 1997

Attest:

BRUCE LEHMAN

Attesting Officer

Commissioner of Patents and Trademarks